United States Patent [19]

Haviv

[11] 4,312,887

[45] Jan. 26, 1982

[54] 2-HYDROXYLAMINOMETHYL PHENOLS

[75] Inventor: Fortuna Haviv, Vernon Hills, Ill.

[73] Assignee: Abbott Laboratories, North Chicago, Ill.

[21] Appl. No.: 954,699

[22] Filed: Oct. 25, 1978

[51] Int. Cl.³ .................... A01N 33/02; C07C 83/00
[52] U.S. Cl. ........................ 424/330; 260/501.17; 424/316; 564/300
[58] Field of Search ............... 260/570.9, 501.17; 424/316, 330; 564/300

[56] References Cited

U.S. PATENT DOCUMENTS

| | | | |
|---|---|---|---|
| 3,546,275 | 12/1970 | Schröter et al. | 260/570.8 X |
| 3,637,854 | 1/1972 | Kyburg et al. | 260/570.8 |
| 3,809,721 | 5/1974 | Schultz et al. | 260/570.9 |
| 3,864,401 | 2/1975 | Schultz et al. | 260/570.9 |
| 3,979,361 | 5/1976 | Schultz et al. | 260/570.9 |
| 4,029,816 | 6/1977 | Cragoe et al. | 424/316 |

*Primary Examiner*—Robert V. Hines
*Attorney, Agent, or Firm*—Robert L. Niblack; Paul D. Burgauer

[57] ABSTRACT

It has been found that certain 4-substituted 2-hydroxylaminomethyl phenols or their nontoxic pharmaceutically acceptable acid addition salts are excellent diuretic, saluretic and anti-inflammatory agents.

24 Claims, No Drawings

2-HYDROXYLAMINOMETHYL PHENOLS

DETAILED DESCRIPTION OF THE INVENTION

Diuretic agents represent an important class of drugs which are effective in the treatment of certain conditions as electrolyte and fluid retention and hypertension. When administered in therapeutic dosages in conventional vehicles, diuretics reduce the amount of alkali metal and chloride ions in the body, lower dangerous excesses of fluid levels to acceptable levels and generally alleviate conditions of edema and hypertension.

A new class of compounds has now been found which exhibits all the above properties and, contrary to some older drugs, exhibit an extremely high therapeutic index, i.e., their efficacy is superior to many drugs currently being used in the field of diuretics. In addition, they produce the highly desirable effect of excreting sodium ions at a much more pronounced rate than potassium ions. Thus, the new compounds are nonkaliuretic diuretics which, in many cases, are effective at oral doses of 0.5 mg./kg. Furthermore, the new compounds are highly effective anti-inflammatories.

The current invention is directed to compounds of the formula

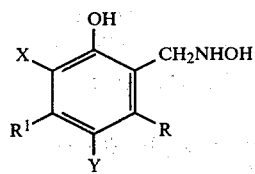

wherein X is hydrogen, halogen, loweralkyl, loweralkyloxy, loweralkylmercapto or trifluoromethyl; Y is chlorine, loweralkyloxy or loweralkyl, R and R' are hydrogen, loweralkyl, loweralkyloxy or chlorine, and nontoxic acid addition salts thereof.

The term "loweralkyl" in this invention is intended to indicate a carbon chain of 1-5 carbons which may be in linear or branched configurations. The term "nontoxic acid addition salts" primarily refers to those salts wherein the above compound of Formula I is associated with hydrochloric, sulfuric, phosphoric, citric, succinic, acetic acid and the like. In some instances, these salts are easy to crystalize from common nontoxic organic solvents, or preferably, from water. However, in the latter instance, the crystals are often associated with between 0.5 and 2.0 molar equivalents of water, i.e., the salts are obtained as hydrates or hemihydrates.

In a general embodiment, the compounds of the current invention are made by introducing the desired substituent X into the 2-position of the appropriately p-substituted phenol. By known methods, the aldehyde group is introduced into the remaining o-position to the hydroxy group of the 4,6-disubstituted or the 4-monosubstituted phenol. In turn, this aldehyde is converted to the corresponding oxime which can be reduced selectively by known chemical means to the corresponding hydroxylaminomethyl compound, i.e., the compound of structure I. When the starting material used above is replaced by 3,4,5-trialkylphenol or 3,5-dichloro-4-alkylphenol, the corresponding compounds of structure I are obtained. As mentioned, one can use 2-trifluoromethyl-4-alkylphenol as the starting material and proceed with the above sequence of reactions by introducing the aldehyde group, etc.

In order to illustrate the method for making the compounds of the current invention, reference is made to the following examples which, however, are not intended to limit the invention in any respect.

EXAMPLE 1

(a) To a stirred solution of 27.6 g. of 4-tert. butylphenol in 225 ml. of chloroform is added dropwise at 0 degrees C., 26.82 g. of sulfuryl chloride. The yellow solution is kept overnight at 5 degrees C. and the solvent and excess reagent are then removed in vacuo. The residue is distilled under reduced pressure to produce 27.2 g. of 4-tert.butyl-2-chlorophenol, b.p. 85–90 degrees C./1 mmHg.

(b) A solution of 64.4 g. of the above and 4.9 g. of hexamethylenetetramine in 500 ml. of trifluoroacetic acid is refluxed for 8 hours. At that time, a solution of 175 ml. of concentrated hydrochloric acid in 250 ml. of water is added dropwise under reflux conditions. The mixture is kept under reflux for 30 minutes and then cooled in an ice bath. The product precipitating from the solution is filtered to give 32.4 g. of yellow crystals which are further purified by sublimation to give pure 3-chloro-5-tert.butylsalicylaldehyde, m.p. 75–77 degrees C.

(c) To a solution of 4.24 g. of material of (b) in 75 ml. of methanol is added a solution of 1.7 g. of hydroxylamine hydrochloride in 25 ml. of water. Subsequently, a solution of 1.325 g. of sodium carbonate in 25 ml. of water is added dropwise. A white precipitate forms under stirring and stirring is continued for 1 hour. The product is then filtered, washed with water and crystallized from hot hexane/cyclohexane to produce 4.15 g. of 3-chloro-5-tert.butylsalicylaldehyde oxime, m.p. 169–170 degrees C.

(d) To a solution of 6.55 g. of the above oxime in 80 ml. of methanol is added under stirring, 5.43 g. of sodium cyanoborohydride. To this mixture is added dropwise a methanol-hydrochloric acid solution at such a rate that a pH of 3.5 is maintained, using bromocresol green as indicator. The solution is stirred for three hours at room temperature after which time the solvent is removed under high vacuum and the residue is dissolved in water. The insoluble material is removed by filtration and the aqueous filtrate is concentrated to give a white powder. This material is extracted with hot ethanol, the extract is evaporated and the white residue is then extracted with ethyl acetate. The insoluble white material is collected and crystallized from ethanol-/ethyl acetate/hexane (about 1:8:1 by volume) to produce 3.32 g. of 2-hydroxylaminomethyl-4-tert.butyl-6-chlorophenol hydrochloride, m.p. 210–212 degrees C.

When the above compound is orally administered at a dose of 50 mg./kg. to rats previously injected with carrageenan in a hind paw (according to Winter et al; Proc. Soc. Exp. Bio. Med., 111, 544 of 1962), the volume of the swelling caused by the carrageenan is reduced by 53%.

When the above starting material, 4-tert.butylphenol is replaced by 25 g. of 3,4,5-trimethylphenol, 2-hydroxylaminomethyl-3,4,5-trimethyl-6-chlorophenol is obtained as a hydrochloride monohydrate in an overall yield of 12% of theory. Its anti-inflammatory effect is similar to that shown in the preceding paragraph.

EXAMPLE 2

To a solution of 31.8 g. of mercuric acetate in 600 ml. of water and 18 ml. of acetic acid is added a warm solution of 21 g. of 4-tert.butylphenol in 30 ml. of ethanol. The mixture is heated at 80 degrees C. for 1 hour, whereby a colorless oil forms that solidifies upon cooling. The supernatant layer is decanted and heated to dissolve the precipitate that forms on slight cooling. A solution of 17.5 g. of sodium chloride in water is added under stirring, precipitating a material which is collected upon cooling. This solid is air-dryed and then dissolved in 900 ml. of 2.5% aqueous sodium hydroxide. The new solution is filtered, acidified with 6 N hydrochloric acid and the white precipitate is collected and dried. All obtained solids are combined, extracted first with boiling ethanol and then with dry benzene and all the extracts are combined and evaporated to produce 11.5 g. of 4-tert.butyl-2-chloromercuryphenol, m.p. 157–160 degrees C. This material is dissolved in 115 ml. of acetic acid and a solution of 7.62 g. of iodine in 50 ml. acetic acid is dropwise added thereto. The initial color of iodine disappears shortly and sodium bisulfite is added to remove any excess iodine. The red precipitate of mercury halide is removed by filtration and the filtrate is poured into water. A red gum which soon solidifies from the mixture is collected, dissolved in ether and the solution again filtered to remove the solid mercury salts. The ether solution is washed with a potassium iodide solution until the washing gives no precipitate with hydrogen sulfide. The ether solution is then dried over sodium sulfate and evaporated to give 7 g. of 4-tert.butyl-2-iodophenol, m.p. 71–73 degrees C.

A solution of 5.5 g. of this material and 2.8 g. of hexamethylenetetramine in 50 ml. of trifluoro acetic acid is heated to 60–65 degrees C. for 4 hours, after which time a mixture of 10 ml. of hydrochloric acid and 5 ml. of water is added dropwise while refluxing is continued for another 30 minutes. The excess acid is then removed in vacuo and the mixture is steam distilled to produce 1.3 g. of 3-iodo-5-tert.butyl-salicylaldehyde, m.p. 72–74 degrees C. The final product is purified by sublimation.

To a solution of 2.91 g. of this material in 35 ml. of methanol is added dropwise a solution of 0.834 g. of hydroxylamine hydrochloride in 10 ml. of water, followed by the dropwise addition of a solution of 0.636 g. of sodium carbonate in 10 ml. of water. Stirring is continued for 1 hour and the precipitate then formed is collected, washed with water and crystallized from hexane to give 2.3 g. of 3-iodo-5-tert.butylsalicylaldehyde oxime, m.p. 157–158.5 degrees C.

To a solution of 5.82 g. of 3-iodo-5-tert.butylsalicylaldehyde oxime in 80 ml. of methanol is added under stirring, 6.284 g. of sodium cyanoborohydride. This mixture is worked up in the fashion described in Example 1(d) except that ether is added to the ethanol extract, precipitating 1.12 g. of 2-hydroxylaminomethyl-4-tert.butyl-6-iodophenol hydrochloride, m.p. 176–178 degrees C.

When the starting material of this Example is replaced with p-ethylphenol, the described procedure produces 2-hydroxylaminomethyl-4-ethyl-6-iodophenol hydrochloride.

EXAMPLE 3

By the previously described method, 2-methyl-4-tert.butylphenol is converted to 3-methyl-5-tert.butylsalicylaldehyde which is purified by distillation; b.p. 90–100 degrees C./0.2 mmHg. In turn, this is treated as shown in Example 1(b) to produce 3-methyl-5-tert.-butylsalicylaldehyde oxime (m.p. 107–108 degrees C.) which converts, according to the above procedures, to 2-hydroxylaminomethyl-4-tert.butyl-6-methylphenol hydrochloride, m.p. 208–210 degrees C.

EXAMPLE 4

A solution of 12.5 g. of 2-trifluoromethylphenol, 6 g. of tert.butylalcohol, 50 ml. of trifluoroacetic acid and 1 ml. of concentrated sulfuric acid is stirred at room temperature for 48 hours. The excess reagent is removed in vacuo and the residue is dissolved in benzene, washed first with aqueous sodium bicarbonate and then with water. The organic phase is dried over sodium sulfate and concentrated. The residue is distilled under high vacuum producing 10 g. of 2-trifluoromethyl-4-tert.butylphenol, b.p. 120–132 degrees C./65 mmHg. This material is treated in the manner described in Example 1(b, c, and d) to produce the aldehyde, its oxime and finally the desired 2-hydroxylaminomethyl-4-tert.butyl-6-trifluoromethyl hydrochloride.

By substituting the 4-tert.butylphenol of Example 1 by an equimolar amount of 3,4-dimethylphenol, 4-n-butyl-2,4-chlorophenol, or 4-methyl-3,6-dichlorophenol and following the above procedure, 2-hydroxylaminomethyl-3,4-dimethyl-6-chlorophenol (m.p. 198–200 degrees C.), 2-hydroxylaminomethyl-4-n-butyl-6-chlorophenol and 2-hydroxylaminomethyl-3,6-dichloro-4-methylphenol are obtained.

EXAMPLE 5

By treating a solution of 4-chloro-3,5-dimethylphenol in accordance with Example 1(b) and steam-distilling the product, 4,6-dimethyl-5-chlorosalicylaldehyde (m.p. 90–92 degrees C.) is obtained. Converting this aldehyde in accordance with Example 1(c and d) produces the corresponding oxime (m.p. 187–190 degrees C.) and finally the 2-hydroxylaminomethyl-3,5-dimethyl-4-chlorophenol hydrochloride; m.p. 206–207 degrees C.

EXAMPLE 6

To a mixture of 37.5 g. of 4-tert.butylphenol, 50 ml. of 60% perchloric acid and 40 ml. of phosphorous oxychloride, cooled to 0 degrees C., is dropwise added 18 ml. of dimethylsulfoxide under vigorous stirring. After 2 hours at 0 degrees, the mixture is stirred 18 hours at room temperature. The formed precipitate is filtered, washed with ice water, air-dried and washed with ether. This material is then added to 500 ml. of a saturated aqueous KCl solution and refluxed for 4 hours. After standing overnight, the oily product is extracted with ether, washed with water and saturated aqueous NaCl and evaporated to produce a colorless oil identified by nmr (CDCl$_3$) as 2-methylmercapto-4-tert.butylphenol.

By proceeding according to Example 1 (b–d), the corresponding aldehyde (m.p. 40–42 degrees C.), oxime (m.p. 93–94 degrees C.) and finally, 2-hydroxylaminomethyl-4-tert.butyl-6-methylmercaptophenol hydrochloride (m.p. 160–162 degrees C.; ethyl acetate/ether) is obtained.

In the same fashion as described above, 2,4-dimethoxyphenol produces 2-hydroxylaminomethyl-4,6-dimethoxyphenol hydrochloride, 2-chloro-4-tert.amylphenol produces 2-hydroxylaminomethyl-4-tert.amyl-6-chlorophenol; 4-methyl-2-trifluoromethylphenol, 4- tert.butyl-2-chloro-5-methoxyphenol, 2-chloro-4-n-pentylphenol and 4-tert.butyl-2-chloro-3,5-dimethoxyphenol, in turn, produce the 2-hydroxylaminomethylphenol hydrochloride with R=R'=H, X=CF$_3$, Y=Me; R=R'=5—MeO, X=Cl, Y=t—Bu; R=R'=H, X=Cl, Y=pentyl; and R=R'=3,5—MeO, X=Cl, Y=t—Bu.

EXAMPLE 7

Oral administration of 2-hydroxylaminomethyl-3,4-dimethyl-6-chlorophenol hydrochloride at a dose of 10 mg./kg. to 8 rats increases the mean 2-hour sodium excretion from 0.65 meq./kg. to 7.56; the corresponding values for potassium are 0.62 to 2.07 and for chlorine 0.84 to 9.17. Urine volume increases from 4.63 to 59.38 ml./kg. In all measurements given, the first numbers shown here are those of the control group with both controls and test groups receiving 50 ml. per kg. of body weight of 0.9% saline and the drug vehicle, said vehicle being a 0.5% aqueous methylcellulose solution, at a rate of 2 ml./kg. of body weight. The control group showed a Na/K excretion ratio of 1.11 while the drug test group showed this ratio at 3.67. The rat-paw edema test of Example 1 shows results similar to those shown there upon oral administration of 50 mg./kg.

The cumulative 6-hour Na/K ratios are 1.58 for the control group (22.31 ml/kg. urine volume) and 3.17 for the test group (73.52 ml/kg.).

The compounds of Examples 1, 2, 3 and 5 produce the following test results upon 1–100 mg/kg. oral administration to rats:

|  | Control | | Compound | |  |
|---|---|---|---|---|---|
|  | 0–2 | 0–6 hrs. | 0–2 | 0–6 hrs. |  |
| I |  |  |  |  |  |
| 10 mg/kg |  |  |  |  |  |
| Urine vol. | 11.67 | 28.71 | 63.62 | 81.93 | ml/kg |
| Sodium | 5.75 | 14.32 | 25.25 | 32.72 | meq/kg |
| Potassium | 3.69 | 7.31 | 5.57 | 7.91 | meq/kg |
| Na/K ratio | 1.61 | 2.01 | 4.60 | 4.17 |  |
| I |  |  |  |  |  |
| 1 mg/kg |  |  |  |  |  |
| Urine vol. | 11.67 | 28.71 | 20.51 | 35.07 | ml/kg |
| Sodium | 5.75 | 14.32 | 7.40 | 13.31 | meq/kg |
| Potassium | 3.69 | 7.31 | 3.86 | 6.32 | meq/kg |
| Na/K ratio | 1.61 | 2.01 | 1.89 | 2.13 |  |
| II |  |  |  |  |  |
| 10 mg/kg |  |  |  |  |  |
| Urine vol. | 4.63 | 22.31 | 70.87 | 95.24 | ml/kg |
| Sodium | 0.65 | 3.38 | 8.92 | 12.06 | meq/kg |
| Potassium | 0.62 | 2.18 | 2.14 | 3.49 | meq/kg |
| Na/K ratio | 1.11 | 1.58 | 4.19 | 3.48 |  |
| III |  |  |  |  |  |
| 10 mg/kg |  |  |  |  |  |
| Urine vol. | 4.63 | 22.31 | 33.79 | 51.76 | ml/kg |
| Sodium | 0.65 | 3.38 | 4.40 | 7.26 | meq/kg |
| Potassium | 0.62 | 2.18 | 1.81 | 2.91 | meq/kg |
| Na/K ratio | 1.11 | 1.58 | 2.43 | 2.53 |  |
| V |  |  |  |  |  |
| 100 mg/kg. |  |  |  |  |  |
| Urine vol. | 4.63 | 22.31 | 33.07 | 49.26 | ml/kg |
| Sodium | 0.65 | 3.38 | 4.24 | 7.09 | meq/kg |
| Potassium | 0.62 | 2.18 | 1.41 | 3.18 | meq/kg |
| Na/K ratio | 1.11 | 1.58 | 3.13 | 2.31 |  |

The compounds of the present invention are preferably used in oral dosage forms such as tablets, capsules, wafers, elixirs, syrups and the like. For liquid forms, the above compounds are suspended in an aqueous medium containing the customary flavoring and coloring agents. Since these compounds are essentially insoluble in water, dispersing and/or suspending agents acceptable for human consumption are used together with suspension stabilizers. For the various solid dosage forms, the usual solid diluents are used where required. Capsules can be filled with undiluted powdered or granulated crystals of the new compounds. For tablets, the following standard procedure may be used:

About one-half of 52 g. of cornstarch is milled together with 10 g. of the new drug and 220 g. of calcium phosphate dibasic dihydrate. This blend is milled until homogenous and passed through a 40-mesh screen. The remaining portion of the cornstarch is granulated with water, heated and mixed with the above drug blend in a hot air oven at 50 degrees C. and sifted through a 16-mesh screen. These granules are then mixed with 16 g. of talcum powder, 4 g. of magnesium stearate and 0.8 g. of combined coloring and flavoring additives. The mixture is blended to homogeneity, passed through a 30-mesh screen and blended for another 15 minutes. This blend is compressed into tablets weighing approximately 300 mg. using a 9/32" standard convex punch resulting in tablets of a hardness of 7–9 with each tablet containing 10 mg. of the drug. In a similar fashion, tablets weighing 320 mg. containing 25 mg. of drug can be prepared, preferably in a tableting machine producing bisected tablets.

A practical range for daily oral administration is between 1.0 and 50 mg./kg. with a preferred range being 3–25 mg./kg. These amounts are based on the free hydroxylamine. However, it is to be understood that pharmaceutically acceptable acid addition salts can be used in place of the free amine, e.g., the hydrochloride, sulfate, phosphate, citrate, succinate, acetate and the like.

I claim:

1. A compound of the formula

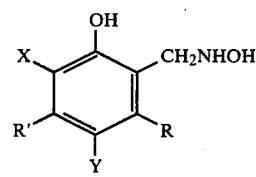

wherein X is hydrogen, halogen, loweralkyl, loweralkyloxy, loweralkylmercapto or trifluoromethyl; Y is chlorine, loweralkyl or loweralkyloxy; R and R' are hydrogen, loweralkyl, loweralkyloxy or chlorine; and nontoxic acid addition salts thereof.

2. A compound of claim 1 wherein Y is tert.butyl.

3. The compound of claim 2 wherein X is chlorine and R and R' are hydrogen.

4. The compound of claim 2 wherein X is methyl and R and R' are hydrogen.

5. The compound of claim 1 wherein X is iodine, Y is ethyl and R and R' are hydrogen.

6. The compound of claim 1 wherein Y is chlorine, X is hydrogen and R and R' are methyl.

7. A medicinal composition for increasing the excretion of urine from warm-blooded animals, containing a compound of the formula

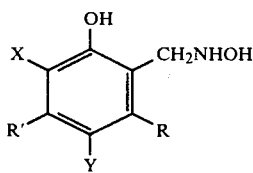

wherein X is hydrogen, halogen, loweralkyl, loweralkyloxy, loweralkylmercapto or trifluoromethyl; Y is chlorine, loweralkyl or loweralkyloxy; R and R' are hydrogen, loweralkyl, loweralkyloxy or chlorine; and nontoxic acid addition salts thereof.

8. A composition according to claim 7 wherein Y is tert.butyl.

9. The composition according to claim 8 wherein X is Cl and R and R' are H.

10. The composition of claim 8 wherein X is methyl and R and R' are H.

11. The composition of claim 7 wherein X is iodine, Y=ethyl and R and R' are H.

12. The composition of claim 7 wherein Y is Cl, X=H and R and R' are methyl.

13. The method of increasing urine excretion in a warm-blooded animal consisting essentially in administering to said animal a diuretically sufficient amount of a compound of the formula

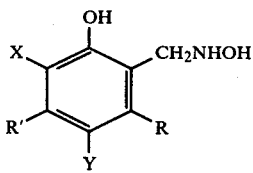

wherein X is hydrogen, halogen, loweralkyl, loweralkyloxy, loweralkylmercapto or trifluoromethyl; Y is chlorine, loweralkyl or loweralkyloxy; R and R' are hydrogen, loweralkyl, loweralkyloxy or chlorine; and nontoxic acid addition salts thereof.

14. The method of claim 13 wherein Y is tert.butyl.

15. The method of claim 14 wherein X is chlorine and R and R' are H.

16. The method of claim 14 wherein X is methyl and R and R' are H.

17. The method of claim 13 wherein X is iodine, Y is ethyl and R and R' are H.

18. The method of claim 13 wherein Y is chlorine, X is H and R and R' are methyl.

19. The method of reducing edema or inflammation in a warm-blooded animal consisting essentially in administering to said animal an anti-inflammatory amount of a compound of the formula

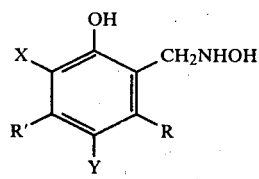

wherein X is hydrogen, halogen, loweralkyl, loweralkyloxy, loweralkylmercapto or trifluoromethyl; Y is chlorine, loweralkyl or loweralkyloxy; R and R' are hydrogen, loweralkyl, loweralkyloxy or chlorine; and nontoxic acid addition salts thereof.

20. The method of claim 19 wherein Y is tert.butyl.

21. The method of claim 20 wherein X is chlorine and R and R' are H.

22. The method of claim 20 wherein X is methyl and R and R' are H.

23. The method of claim 19 wherein X is iodine, Y is ethyl and R and R' are H.

24. The method of claim 19 wherein Y is chlorine, X is H and R and R' are methyl.

* * * * *